United States Patent [19]
Milanovich

[11] Patent Number: 5,439,377
[45] Date of Patent: Aug. 8, 1995

[54] BI-DIRECTIONAL ORTHODONTIC APPLIANCE

[76] Inventor: Philip J. Milanovich, 10 N. Lake Dr., Butte, Mont. 59701

[21] Appl. No.: 230,762

[22] Filed: Apr. 21, 1994

[51] Int. Cl.⁶ .............................................. A61C 3/00
[52] U.S. Cl. .................................................. 433/7
[58] Field of Search ............... 433/7, 18, 24; 254/233, 254/234

[56] References Cited

U.S. PATENT DOCUMENTS

| | | | |
|---|---|---|---|
| 836,918 | 11/1906 | Bucy | 254/234 |
| 917,407 | 4/1909 | Blauvac | 254/234 |
| 3,800,240 | 4/1974 | Ouakmine | 433/7 |
| 4,347,054 | 8/1982 | Kraus et al. | 433/7 |
| 4,482,318 | 11/1984 | Forster | 433/7 |
| 4,571,177 | 2/1986 | Dahan | 433/7 |
| 5,002,485 | 3/1991 | Aagesen | 433/7 |
| 5,133,659 | 7/1992 | Shilliday | 433/3 |

FOREIGN PATENT DOCUMENTS

| | | | |
|---|---|---|---|
| 0083906A1 | 7/1983 | European Pat. Off. | A61C 7/00 |
| 2378501 | 9/1978 | France | 433/7 |
| 2656693 | 6/1978 | Germany | 433/7 |
| 2703820 | 8/1978 | Germany | 433/7 |
| 3241105 | 5/1984 | Germany | 433/7 |

Primary Examiner—Nicholas D. Lucchesi
Attorney, Agent, or Firm—Jacobson, Price, Holman & Stern

[57] ABSTRACT

In an orthodontic appliance, two halves of a jack body are connected by a screw and have parallel rods with tooth-encircling bands. Each half of the jack body includes an extension connected to the body by an adjustment mechanism for moving the extension perpendicularly to the jack screw. The extensions can be located on the same side of the jack body on opposite sides of the jack body, or on both sides of the jack body. The halves of the jack body are separated by rotating an adjuster connected to the jack screw. The extensions are moved by the respective adjustment mechanism. In an alternative embodiment of the invention, the jack screw is separated into opposed screws.

13 Claims, 6 Drawing Sheets

BI-DIRECTIONAL ORTHODONTIC APPLIANCE

BACKGROUND OF THE INVENTION

This invention relates to orthodontic appliances and, in particular, to an orthodontic appliance for controlling the movement of teeth in one or more directions.

Malocclusion, the misalignment of the maxillary (upper) and mandibular (lower) teeth when the jaw is closed, is a common problem usually occurring with the eruption of the permanent teeth. If left untreated, malocclusion can lead to headaches, disfigurement, deformation of the jaw, premature wearing of the teeth, and eventual tooth loss.

There are many appliances available to an orthodontist or correcting malocclusion. One type of appliance uses a mall screw jack attached to selected maxillary teeth. A problem with such an appliance is the limited motion available from the screw jack, i.e. motion is limited to a direction parallel to the length of the screw.

Although the human body is generally characterized as having bilateral symmetry, there are asymmetries in any given individual. In the mouth, the causes of malocclusion are rarely symmetrical and implicit in existing orthodontic appliances is an oral symmetry that often does not exist in fact. Because of asymmetries, the corrective movement of each tooth must be controlled by a combination of treatments with different appliances. If the appliances must be used consecutively, the treatment of a patient is prolonged.

Asymmetry is not the only reason appliances may have to be used consecutively. Class II malocclusion is the most common and usually occurs because the mandible (jaw one) is recessive, i.e. positioned further back than it ought to be, giving the appearance of protruding front teeth. The typical treatment is to expand the maxillary arch and advance the mandible. A problem with this technique is that opposing molars may become misaligned, unless the molars are distalized (moved further back in the mandible). In order to complete the treatment, two consecutive appliances are necessary: a first appliance to advance the mandible and expand the arch and a second appliance to distalize the molars. The second appliance is often the "headgear" seen on young adolescents A problem with headgear, or with any removable appliance, is the need for compliance by the patient. Unless instructions are followed faithfully, treatment becomes an approximation of the orthodontist's program.

Another problem with headgear is that it operates on both sides of the mouth simultaneously. A difficult problem is known as a Class II subdivision. "Subdivision" refers to the fact that the teeth are not symmetrically positioned relative to a median line through the mouth. For example, the teeth on the right side of the mouth are in the correct biting position and the cuspid and/or eye tooth are out of position in the left side of the mouth. Expanding the maxillary arch and using headgear will distalize the molars on both sides of the mouth.

A particularly difficult Class II subdivision is when a tooth erupts in the palate rather than in the arch. It is difficult to move such a tooth into the arch. First the tooth has to be extruded or forced into the arch and then tipped into the correct position. For example, if a cuspid erupts in the palate and the root must be moved into the buccal plate, correction may take six months to a year just to complete this one process.

Tipping of teeth also occurs as a result of banding, wherein an anchor is bonded to each tooth and the anchors are interconnected with a wire. As the teeth move, they tip. The initial wire is then replaced with a rectangular wire and the teeth are torqued into position.

Expanding the maxillary arch opens the sutures or joints between the places of the skull, e.g. the midpalatine suture, the frontal nasal suture, and the zygomatic suture. These sutures do not open in the sense of forming a gap but grow together as the places are forced part. In patients with a cleft palate, there is no bony union. It is tissue and expanding the suture can tear the tissue. What is sometime desired is an appliance which can serve as a platform for holding the teeth in position during reconstruction.

Some older patients have patent sutures, i.e. sutures at are locked and cannot be activated. A surgeon either opens the suture with a hematome or scores the maxillary arch by cutting through the maxillary sinus in segmenting the arch. It is desirable to activate the suture while it segmented, move the segments into the desired position, and then fix the segments in place.

All of the procedures described above take time and can be combined in various ways, depending upon the needs of the patient, for a complete treatment that can take from eighteen to thirty months.

In view of the foregoing, it is therefore an object of the invention to provide an orthodontic appliance for moving teeth in more than one direction simultaneously.

Another object of the invention is to provide an orthodontic appliance for asymmetrical correction of malocclusion.

A further object of the invention is to provide an orthodontic appliance which can move teeth without tipping.

Another object of the invention is to provide an orthodontic appliance which can do simultaneous processes that were formerly done sequentially.

A further object of the invention is to provide an orthodontic appliance which can serve as a platform for positioning segments during reconstruction of the palate.

SUMMARY OF THE INVENTION

The foregoing objects are achieved in the invention in which two halves of a jack body are connected by guide bars and an adjustment screw mechanism. Each half of the jack body includes an extension connected to the body by a rack and pinion, worm gear or screw jack mechanism for moving the extension perpendicularly to the jack screw. The extensions can be located on the same side of the jack body or on opposite sides of the jack body. Alternatively, each half of the jack body can have two extensions on opposite sides of the jack body, respectively. The halves of the jack body are separated by rotating an adjuster connected to the adjustment mechanism, conveniently a jack screw. The or each extension is moved by rotating the respective pinion, worm or screw jack. In an alternative embodiment of the invention, the jack screw between the halves may be separated into opposed screws.

BRIEF DESCRIPTION OF THE DRAWINGS

A more complete understanding of the invention can be obtained by considering the following detailed description in conjunction with the accompanying drawings, wherein like reference numerals are used to depict like parts and in which.

DETAILED DESCRIPTION OF THE INVENTION

Figures 1, 2:
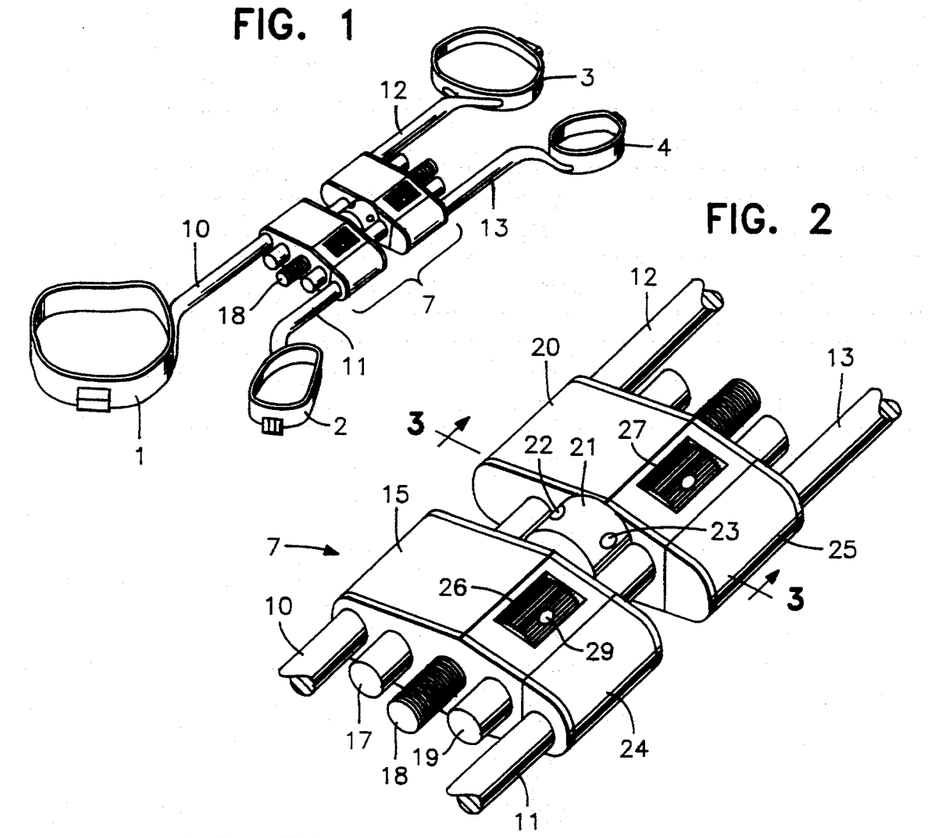
FIG. 1 illustrates a bi-directional orthodontic appliance constructed in accordance with a preferred embodiment of the invention.
FIG. 2 is a perspective view of the jack body from the appliance shown in FIG. 1.

FIG. 1 is a perspective view of an orthodontic appliance constructed in accordance with a preferred embodiment of the invention. In FIG. 1, jack body 7 has rods 10, 11, 12 and 13, extending from each corner of the jack body in a direction parallel to the length of jack screw 18. Tooth attachment means in the form of bands 1, 2, 3, and 4 are attached to respective ends of the rods for attaching the appliance to a patient's teeth. In accordance with the invention, each of bands 1, 3, and 4 can be moved independently of the others to suit the needs of the patient. Some of the specific movements available are described in connection with FIGS. 5 and 6. In general, bands 1 and 2 are moved away from bands 3 and 4 and bands 2 and 4 can be moved independently of each other away from bands 1 and 3. The bands 1, 2, 3, 4 can be supplemented or replaced by tooth attachment bonds.

Jack body 7, shown in greater detail in FIG. 2, includes four parts, base part 15 having rod 10 attached at one end thereof and including guide bar 17, jack screw 18, and guide bar 19. Rod 10 is press fit or otherwise permanently attached to base part 15. Guide bars 17 and 19 fit closely within holes in base part 15 but are free to move longitudinally in a direction parallel to jack screw 18. Jack screw 18 fits within a threaded bore in base part 15.

Base part 20 is similarly constructed and has rod 12 permanently attached at one end thereof. Guide bars 17 and 19 pass through bores in base part 20 and jack screw 18 engages a threaded bore in base part 20. Between base parts 15 and 20 is adjuster 21 which is attached to jack screw 18 at the approximate midpoint thereof and includes a plurality of holes, such as holes 22 and 23, located approximately every ninety degrees around adjuster 21. A suitable tool engages one of the holes in adjuster 21 for rotating adjuster 21 and spreading base parts 15 and 20. The shanks of jack screw 18 on either side of adjuster 21 have opposite threads and rotation of adjuster 21 causes base parts 15 and 20 either to separate or to draw together. The width of adjuster 21 determines the minimum separation of base parts 15 and 20.

Extension part 24 is attached to base part 15 by a rack (not shown in FIG. 1) which engages pinion 26 contained in base part 15. Similarly, extension 25 is attached to base part 20 by a rack engaging pinion 27. The pinions include a plurality of holes such as hole 29 for engaging a suitable tool to rotate the pinions and to extend or retract the respective extension part. Extension part 24 has rod 11 permanently attached thereto and extension 25 has rod 13 permanently attached thereto. Thus the base part and an extension form a pair of parts which are moved together by jack screw 18. The extensions are individually adjustable by actuating pinion 26 or pinion 27.

Figure 3A:
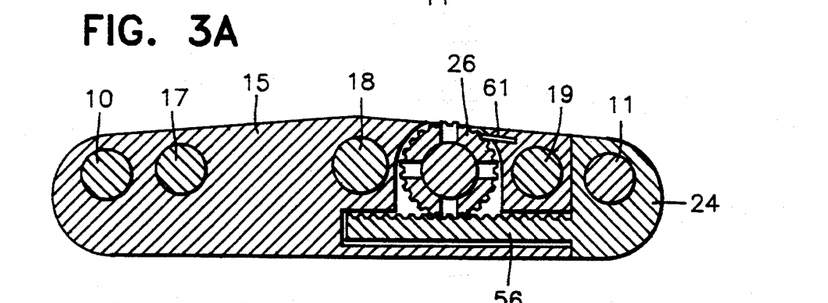
FIG. 3A is a cross-section taken along line 3—3 in FIG. 2 showing the extension in a closed position.

FIG. 3A is a cross-section along line 3—3 in FIG. 3. In FIG. 3A, pinion 26 engages rack 56 and is held in place by ratchet 61. In a preferred embodiment of the invention, ratchet 61 is simply a small blade of spring steel mounted in the body of base part 15 and extending to the perimeter of pinion 26 to engage the toothed surface of pinion 26. As illustrated in FIG. 3A, pinion 26 can rotate counterclockwise but cannot rotate clockwise because of ratchet 1. Ratchet 61 can be lifted away from pinion 26 by an orthodontist using a suitable tool.

Figure 3B:
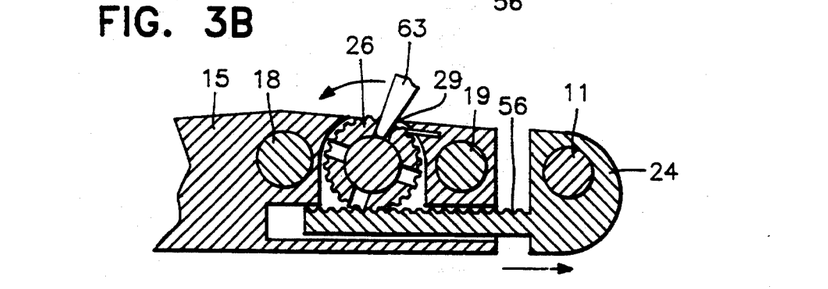
FIG. 3B illustrates the extension in an open position.

FIG. 3B illustrates extension 24 moving to an open position as pick 63 rotates pinion 26 in the direction indicated. The length of rack 56 is a matter of design and determines the maximum amount of travel for extension 24.

Figure 4:
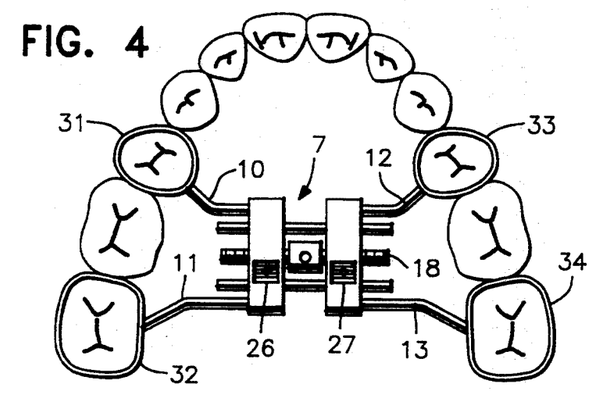
FIG. 4 illustrates an appliance installed with the jack screw perpendicular to the median line of the mouth.

FIG. 4 illustrates one configuration for mounting jack body 7 in the mouth of a patient. In FIG. 4, rod 10 is attached to band 31 around one tooth on the right side of the mouth and band 33 is attached to the corresponding tooth on the left side of the mouth. Similarly, rod 11 is attached by band 32 to a molar on the right side of the mouth and rod 13 is attached by band 34 to the corresponding molar on the left side of the mouth. The bands are rigidly held by the rods and the teeth cannot tip as they are being moved. This shortens treatment time since moving and tipping are done sequentially in the prior art.

FIG. 4 is but one example of how jack body 7 can be attached to the teeth. In actual practice the tooth or teeth chosen to be attached to the respective rods depends upon the correction to be made. In addition, while each rod is illustrated as attached to a single tooth, it is understood that one or all of the rods can be attached to a group or segment of teeth.

As illustrated in FIG. 4, jack screw 18 is transverse to the maxillary arch and rotation of jack screw 18 will cause expansion of the maxillary arch. At the same time, actuation of pinions 26 or 27 will distalize the molars. In accordance with the invention, one can actuate a single pinion, thereby distalizing the molars on one side of the mouth while not distalizing the molars on the other side of the mouth. This ability to expand the maxillary arch and simultaneously to distalize the molars enables one to significantly shorten the treatment period for the patient.

FIG. 4 illustrates but one application of the bi-directional orthodontic appliance of the invention. The appliance can be installed with jack screw 18 parallel to the median line of the mouth rather than perpendicular to the median line of the mouth. In this configuration, actuation of jack screw 18 distalizes the molars on both sides of the mouth by the same amount. In this alternative installation, individual teeth can be moved by manipulating the pinion to control the position of the extension part. In this way, for example, a cuspid that has erupted in the palate can be moved into the maxillary arch at the same time that the molars are distalized.

Figures 5A, 5E:
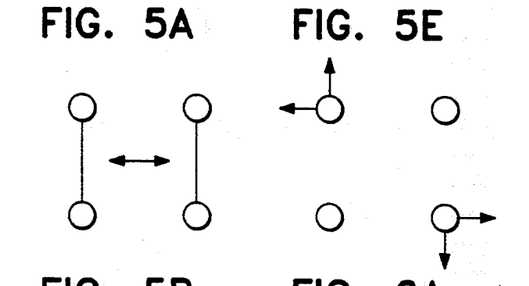
FIGS. 5A–5E schematically illustrates several of the movements available from a bi-directional orthodontic appliance constructed in accordance with the invention.
Figure 5B:
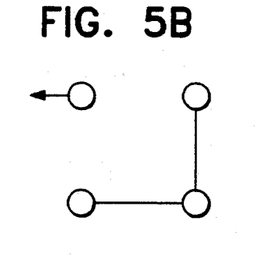
Figure 5C:
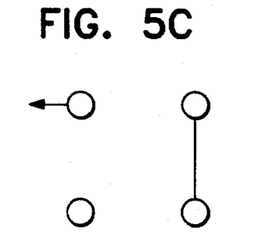
Figure 5D:
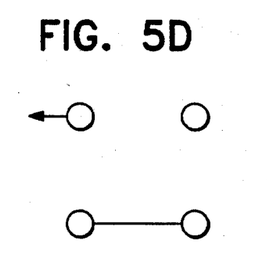

There are a number of distinct movements that can be obtained from the appliance of the invention. FIGS. 5A–5E illustrates five basic movements for treating patients. In FIG. 5A, the teeth on either side of the mouth are joined in a segment and the maxillary arch is expanded. In FIG. 5B, two teeth on one side of the mouth are joined to a third on the other side of the mouth forming a solid anchor or the outward or buccal movement of a fourth tooth. In FIG. 5C, the teeth on one side of the mouth are joined together and a tooth on the opposite side of the mouth is moved outwardly, i.e. perpendicular to the segment. In FIG. 5D, a tooth on one side of the mouth is joined to a tooth on the opposite side of the mouth and one of the anterior teeth is moved outwardly, i.e. parallel to the segment. In FIG. 5E, diagonally opposite teeth are moved. The motions illustrated in FIGS. 5A–5E are not exhaustive of the motions available.

Figure 6A:
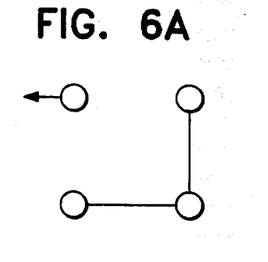
FIGS. 6A–6H illustrates rotations and reflections of the movement illustrated in FIG. 5B.
Figure 6B:
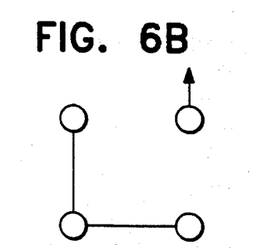
Figure 6C:
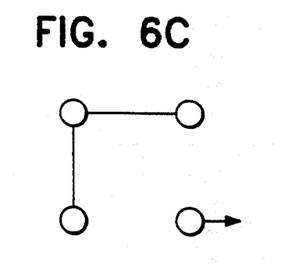
Figure 6D:
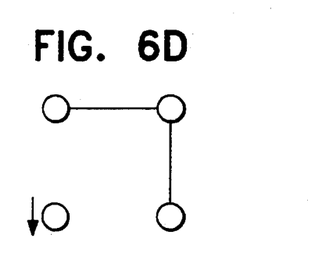
Figure 6E:
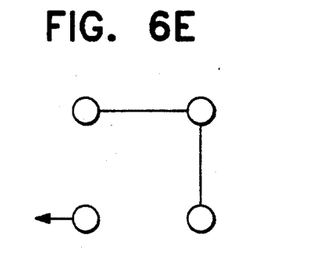
Figure 6F:
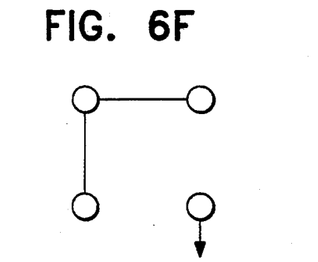
Figure 6G:
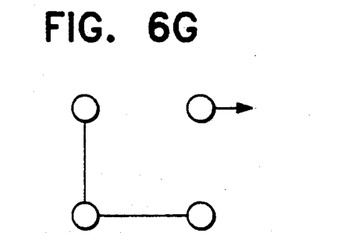
Figure 6H:
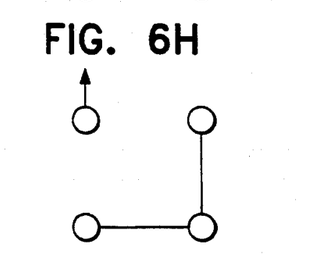

FIGS. 6A–6H illustrate eight different movements obtainable by rotating and reflecting FIG. 5B. FIG. 6A is the same as FIG. 5B. FIG. 6B is FIG. 6A rotated clockwise by ninety degrees. FIG. 6C is FIG. 6B rotated clockwise by ninety degrees. FIG. 6D is FIG. 6C rotated clockwise by ninety degrees. FIGS. 6E–6H are reflections of FIGS. 6A–6D about a line underneath FIGS. 6A–6D, respectively.

Similar rotations and reflections can be done with the movements shown in FIGS. 5C and 5D. For FIGS. 5A and 5E, rotation and reflection are the same. Thus, there are a wide variety of movements available and, further, these movements can be combined to provide the appropriate treatment for a patient. The flexibility obtainable from an appliance constructed in accordance with the invention enables the orthodontist to reduce the treatment time for the patient or to provide a more complex treatment than has been obtainable from appliances of the prior art.

Figure 7:
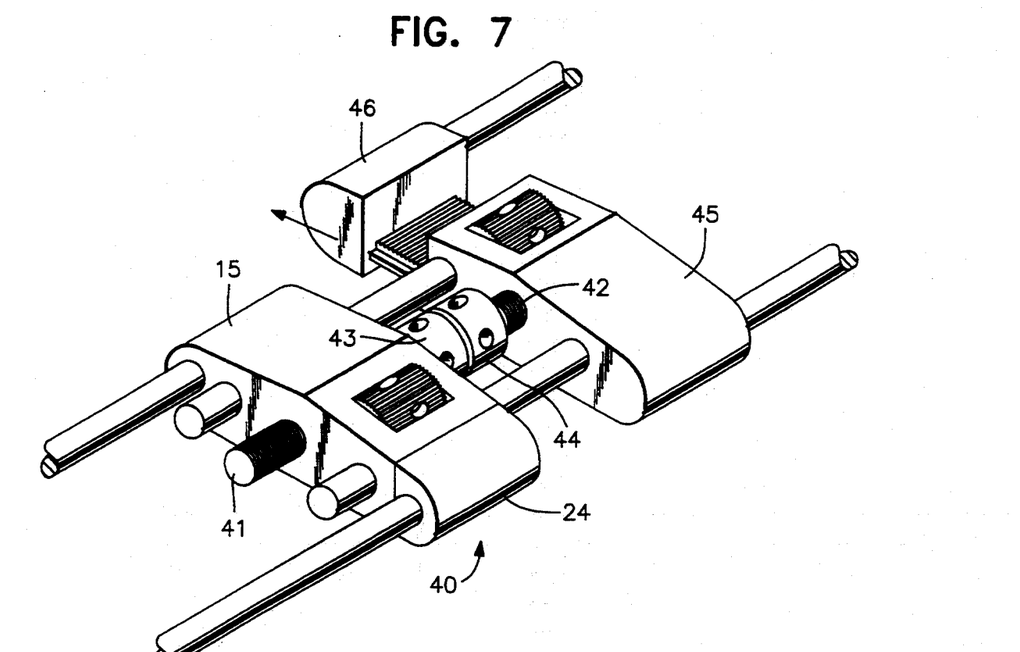
FIG. 7 illustrates a bi-directional orthodontic appliance constructed in accordance with an alternative embodiment of the invention.

FIG. 7 illustrates an alternative embodiment of the invention in which the jack screw includes two separate screws having their heads adjacent each other and the shank of the screws extending oppositely into respective halves of jack body 40. Specifically, jack screw 41 extends through base part 15 and terminates in adjuster 43. Jack screw 42 extends through base part 45 and terminates in adjuster 44. Adjusters 43 and 44 are the caps of jack screws 41 and 42, respectively.

An advantage of this embodiment is that the halves of jack body 40 need not be positioned prior to installation. For example, during installation adjusters 43 and 44 can be spaced slightly apart and later rotated to be brought into contact for forcing the halves of jack body 40 apart. This is particularly useful for example during reconstructive surgery where movement of the plates in the skull would be impaired by the appliance permanently locating the teeth to which it was attached. In addition, one can adjust the location of jack body 40 to be off-center within the mouth by suitable adjustment of jack screws 41 and 42.

The embodiment illustrated in FIG. 7 also differs from the embodiment illustrated in FIG. 2 in the location of extension 46 relative to base part 45. In the embodiment of FIG. 2, the extensions are on the same side of jack screw 18. In the embodiment of FIG. 7, the extensions are on opposite sides of jack screws 41 and 42, which enhances the ability of the orthodontist to treat Class II subdivision (asymmetric) malocclusions.

Figure 8:
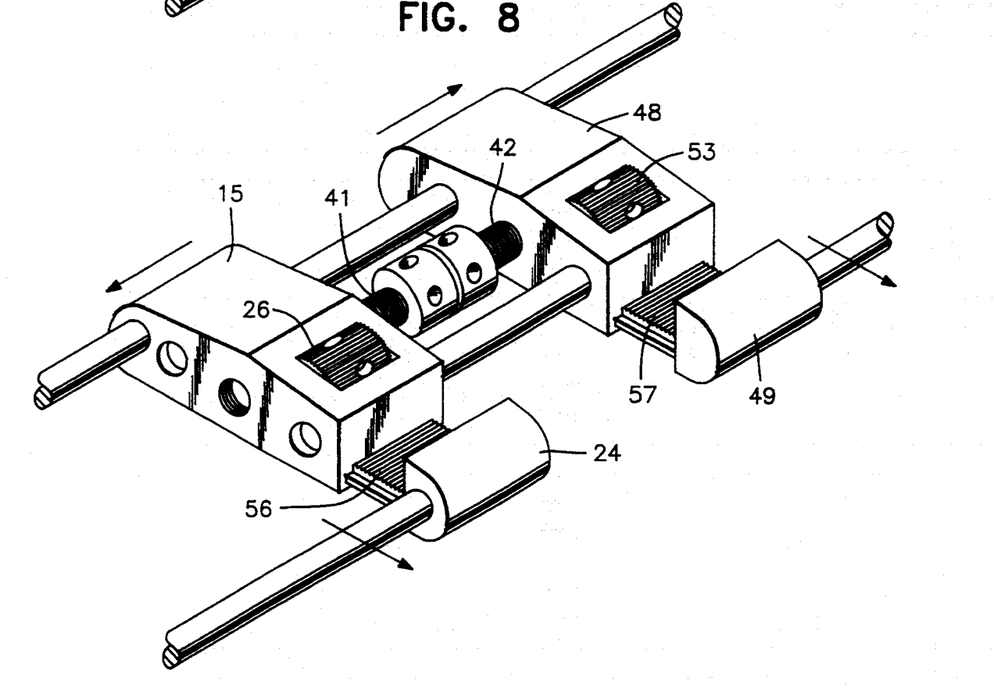
FIG. 8 illustrates a modification of the appliance illustrated in FIG. 7.

In FIG. 8, extension parts 24 and 49 are located on the same side of jack screws 41 and 42 and are connected to pinions 26 and 53 by racks 56 and 57, respectively. This orientation enables the motion illustrated in FIG. 5E, for example.

Figure 9:
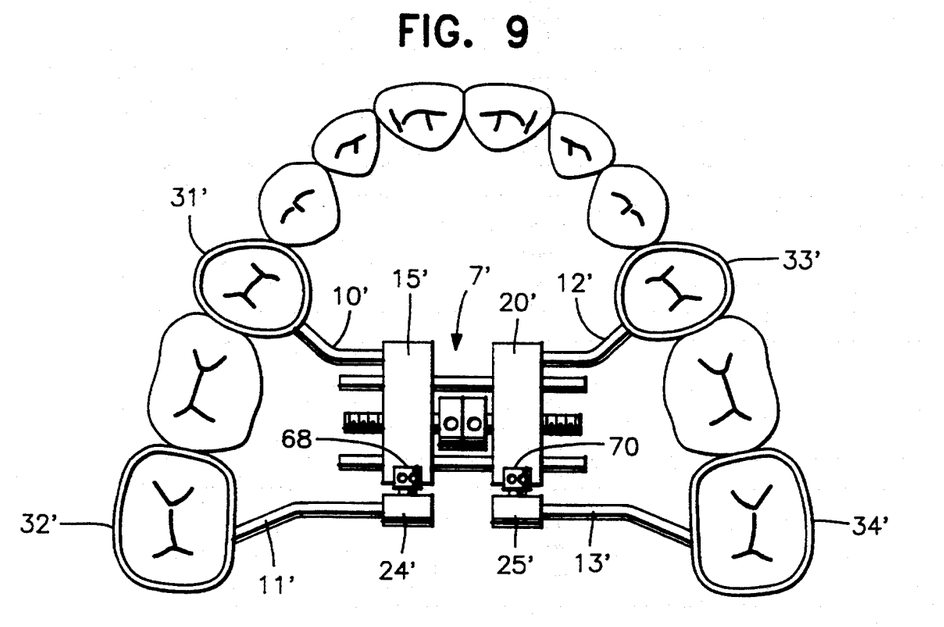
FIG. 9 is a view similar to FIG. 4 showing the use of an appliance constructed in accordance with another embodiment of the invention.
Figure 10A:
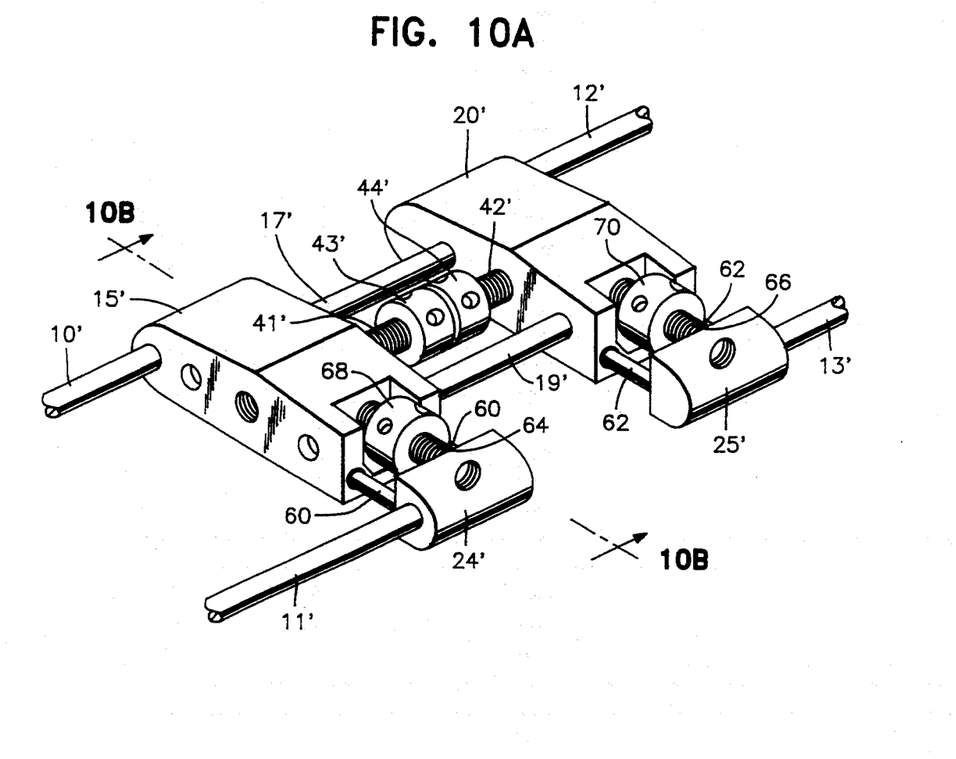
FIG. 10A is a perspective view of the jack body of the appliance shown in FIG. 9.
Figure 10B:
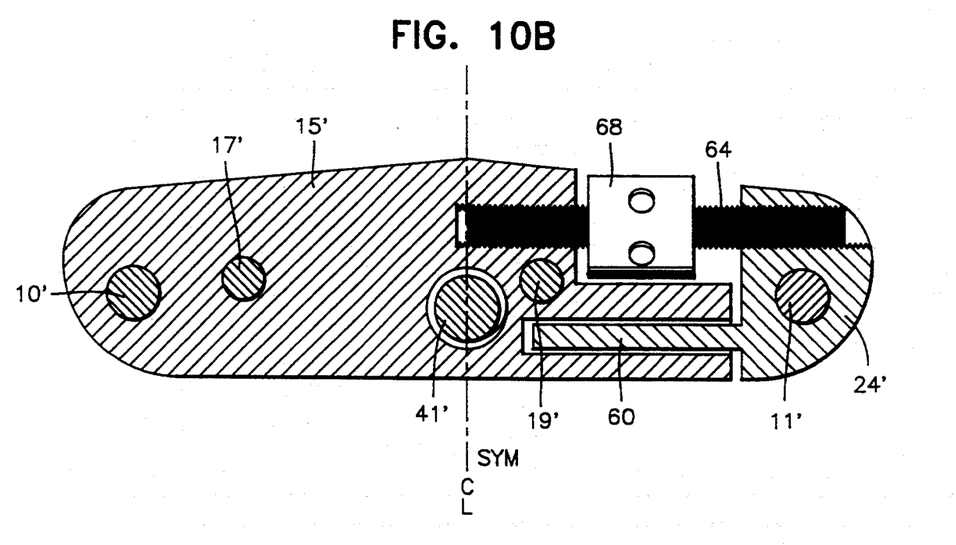
FIG. 10B is a cross-sectional view on line 10B—10B in FIG. 10A.

FIGS. 9, 10A and 10B show another embodiment of the invention similar to the embodiments shown in FIGS. 7 and 8 insofar as the respective halves 15′, 20′ are separated and adjusted by means of a pair of screws 41′, 42′ with individual adjustors 43′, 44′. In this embodiment, however, different mechanisms are provided for moving the extensions 24′, 25′ which are shown on the same side of the jack body. Thus, in place of the rack and pinion mechanisms of the previous embodiments, in this case the extensions are fixed on guide bars 60, 62 (suitably spaced from guide bars 17′, 19′, see FIG. 10B) and the jack halves and extensions are fitted with jack screws 64, 66 and adjusters 68, 70 similar in structure to jack screw 18 and adjuster 21 shown in FIGS. 1–4 so that the extensions, in this case are adjusted in like manner to the jack halves themselves. As shown in FIG. 9, the appliance is used in like manner to those previously described.

In place of the jack screw mechanisms for moving the extensions, worm and wheel arrangements (not shown) can also be used, and the extensions 24′, 25′ could be on opposite sides of the jack body.

Figure 11:
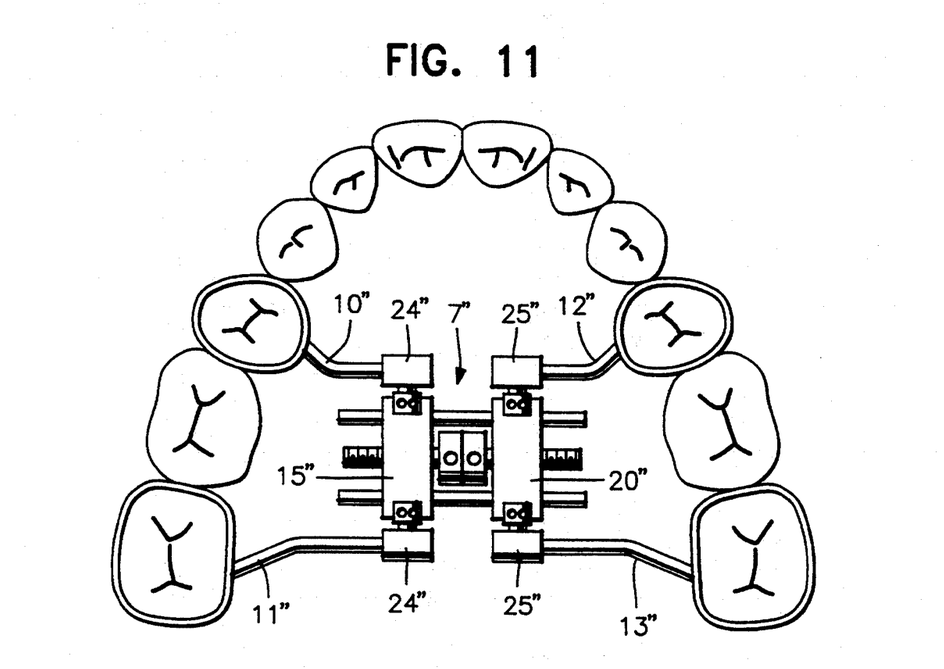
FIG. 11 is a view similar to FIGS. 4 and 9 showing the use of an appliance constructed in accordance with still another embodiment of the invention.
Figure 12:
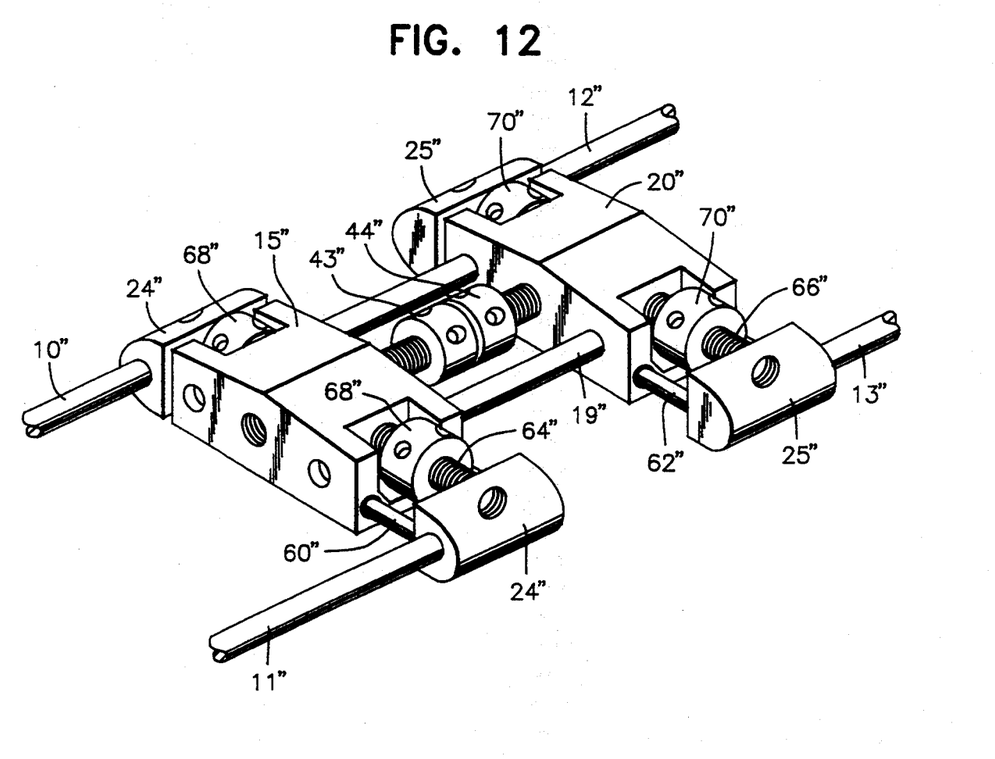
FIG. 12 is a perspective view of the jack body of the appliance shown in FIG. 11.

FIGS. 11 and 12 show an embodiment of the invention similar to that shown in FIGS. 9 and 10, except that in this case, each half of the jack body 15″, 20″ is provided with a pair of extensions 24″ and 25″ on opposite sides of the body, the extensions again being adjusted by jack screws and adjusters 64″, 68″ and 66″, 70″. In this case, each of the rods 10″, 11″, 12″ and 13″ is attached to one of the extensions. It is evident from FIG. 12 that the appliance is used in like manner to those previously described but this embodiment has a greater range of adjustment for the individual teeth to which it is applied.

The invention thus provides an orthodontic appliance for moving teeth in more than one direction simultaneously permitting correction of asymmetrical malocclusion in less time than previously required. The teeth can be moved without tipping and, in general, an orthodontic appliance constructed in accordance with the invention can do simultaneous processes that were formerly done sequentially. In addition, the appliance can serve as a platform for positioning segments during reconstruction of the palate.

In each of the illustrated embodiments, the holes in the various pinions used for inserting tools used for moving the extensions or jack halves, may be color coded or otherwise distinguished to assist a patient in following a prescribed routine for in situ adjustments of the appliance.

Having thus described the invention, it will be apparent to those of skill in the art that various modifications can be made within the scope of the invention. For example, the particular shape for the jack body is not critical and can be modified to suit the needs of a patient. For example, the jack body can be made smaller by eliminating one of the guide bars.

It is preferable for the adjusters, such as adjuster 21, 26, 27, 53, 68 and 70 to be operated in the anterior posterior direction.

What is claimed is:

1. A bi-directional orthodontic appliance comprising:
    a split jack body having a first half and a second half;
    parallel rods attached to and extending from the respective halves, the rods having outer ends for tooth attachment means;
    a jack screw means connecting said first half to said second half allowing movement of the respective halves towards and away from one another, said jack screw means extending in a first direction parallel to said rods;
    wherein at least one of said halves includes an extension connected to said at least one of said halves on one side of said jack screw means by an adjustment mechanism; and
    wherein said extension is movable by said adjustment mechanism in a second direction, different from said first direction and wherein one of said rods is fitted to said extension, whereby said appliance can apply asymmetric corrective movements to maxillary teeth.

2. The appliance as set forth in claim 1 wherein each half includes an extension and each extension is fitted with one of said rods.

3. The appliance as set forth in claim 2 wherein said extensions are positioned on the same side of said jack screw means.

4. The appliance as set forth in claim 2 wherein said extensions are positioned on opposite sides of said jack screw means.

5. The appliance as set forth in claim 1 wherein said adjustment mechanism comprises a rack and pinion for moving the extension.

6. The appliance as set forth in claim 1 and further including guide bars parallel to said jack screw means and interconnecting said first half and said second half.

7. The appliance as set forth in claim 1 wherein said jack screw means includes a pair of screws having adjoining heads and shanks extending away from said heads into respective halves of said jack body, whereby said appliance can be positioned after attachment to teeth.

8. The appliance as set forth in claim 1 wherein said at least one of said halves includes a further extension on an opposite side of said jack screw means, said further extension being movable in said second direction and wherein another of said rods is fitted to said further extension.

9. The appliance as set forth in claim 8 wherein each of said halves includes a pair of extensions on opposite sides of said jack screw means respectively, said extensions each being movable in said second direction and each being fitted with one of said rods.

10. The appliance as set forth in claim 1 wherein said adjustment mechanism comprises a jack screw and adjuster for moving the extension and guide bars carrying the extension.

11. The appliance as set forth in claim 1 wherein said jack screw means comprises a jack screw and adjuster.

12. The appliance as set forth in claim 1 wherein the outer ends of the rods are provided with tooth attachment means.

13. The appliance as set forth in claim 12 wherein the tooth attachment means includes a tooth encircling band on the outer end of each rod.

* * * * *